US00PP34221P2

(12) United States Plant Patent
Westendorp

(10) Patent No.: US PP34,221 P2
(45) Date of Patent: May 10, 2022

(54) ***ANEMONE* PLANT NAMED 'WESKIPO'**

(50) Latin Name: ***Anemone hupehensis* Lemoine.**
Varietal Denomination: WESKIPO

(71) Applicant: Westendorp V.O.F., Klijndijk (NL)

(72) Inventor: Andre Westendorp, Klijndijk (NL)

(73) Assignee: Westendorp V.O.F., Klijndijk (NL)

( * ) Notice: Subject to any disclaimer, the term of this patent is extended or adjusted under 35 U.S.C. 154(b) by 0 days.

(21) Appl. No.: 17/300,881

(22) Filed: Dec. 6, 2021

(30) Foreign Application Priority Data

Dec. 6, 2020 (QZ) ..... PBR 2020/3193

(51) Int. Cl.
*A01H 6/72* (2018.01)
*A01H 5/02* (2018.01)

(52) U.S. Cl.
USPC ..... Plt./263.1

(58) Field of Classification Search
USPC ..... Plt./263.1
See application file for complete search history.

*Primary Examiner* — Annette H Para
(74) *Attorney, Agent, or Firm* — Samuel R. McCoy, Jr.

(57) ABSTRACT

'WESKIPO' is a new and distinctive *Anemone hupehensis* plant which is characterized by a compact growth habit, durable foliage, and strong flowering stems which bear very-double, light pink flowers. The new variety propagates successfully by cuttings and tissue culture and has shown to be uniform and stable in the resulting generations from asexual propagation.

3 Drawing Sheets

Latin name of the genus and species: The Latin name of the genus and species of the novel variety disclosed herein is *Anemone hupehensis* Lemoine.

Variety denomination: The inventive variety of *Anemone* disclosed herein has been given the variety denomination 'WESKIPO'.

CROSS REFERENCE TO RELATED APPLICATIONS

This application claims priority to the Community Plant Variety Rights application number 2020/3193, filed Dec. 6, 2020, which is herein incorporated by reference.

BACKGROUND OF THE INVENTION

Parentage: 'WESKIPO' is the result of a controlled cross-pollination breeding program carried out by the inventor at their commercial nursery in Klijndijk, The Netherlands. The inventor began by performing a controlled self-pollination of *Anemone hupehensis* 'Lorelei' (unpatented). Seed from the controlled pollination of 2017 cross was harvested, then germinated, and the resulting seedlings were then grown to a mature size. In 2016, the inventors selected the new *Anemone* cultivar due to its unique flower characteristics. This new and distinctive cultivar was given the name 'WESKIPO'.

Asexual Reproduction: Asexual reproduction of 'WESKIPO' was first accomplished in October of 2017 by way of root cuttings at the inventor's nursery in Klijndijk, The Netherlands. 'WESKIPO' was subsequently asexually reproduced by way of meristematic tissue culture micro propagation. Seventeen successive generations have shown that the unique features of the instant cultivar are stable and reproduce true to type.

SUMMARY OF THE INVENTION

The cultivar 'WESKIPO' has not been observed under all possible environmental conditions and the phenotype may vary somewhat with variations in the instant environment such as temperature, day length, and light intensity, without, however, any variance in genotype. The following characteristics have been repeatedly observed and represent the distinguishing characteristics of the new *Anemone* cultivar, 'WESKIPO'. These traits, in combination, distinguish 'WESKIPO' as a new and distinct cultivar.

1. *Anemone* 'WESKIPO' exhibits a compact growth habit; and
2. *Anemone* 'WESKIPO' exhibits strong, durable foliage and flowering stems; and
3. *Anemone* 'WESKIPO' exhibits very-doubled, apetalous flowers with an abundance of tepaloids; and
4. *Anemone* 'WESKIPO' exhibits light purple flowers, generally appearing as a pale pink color.

BOTANICAL DESCRIPTION OF THE PLANT

Figure 1:
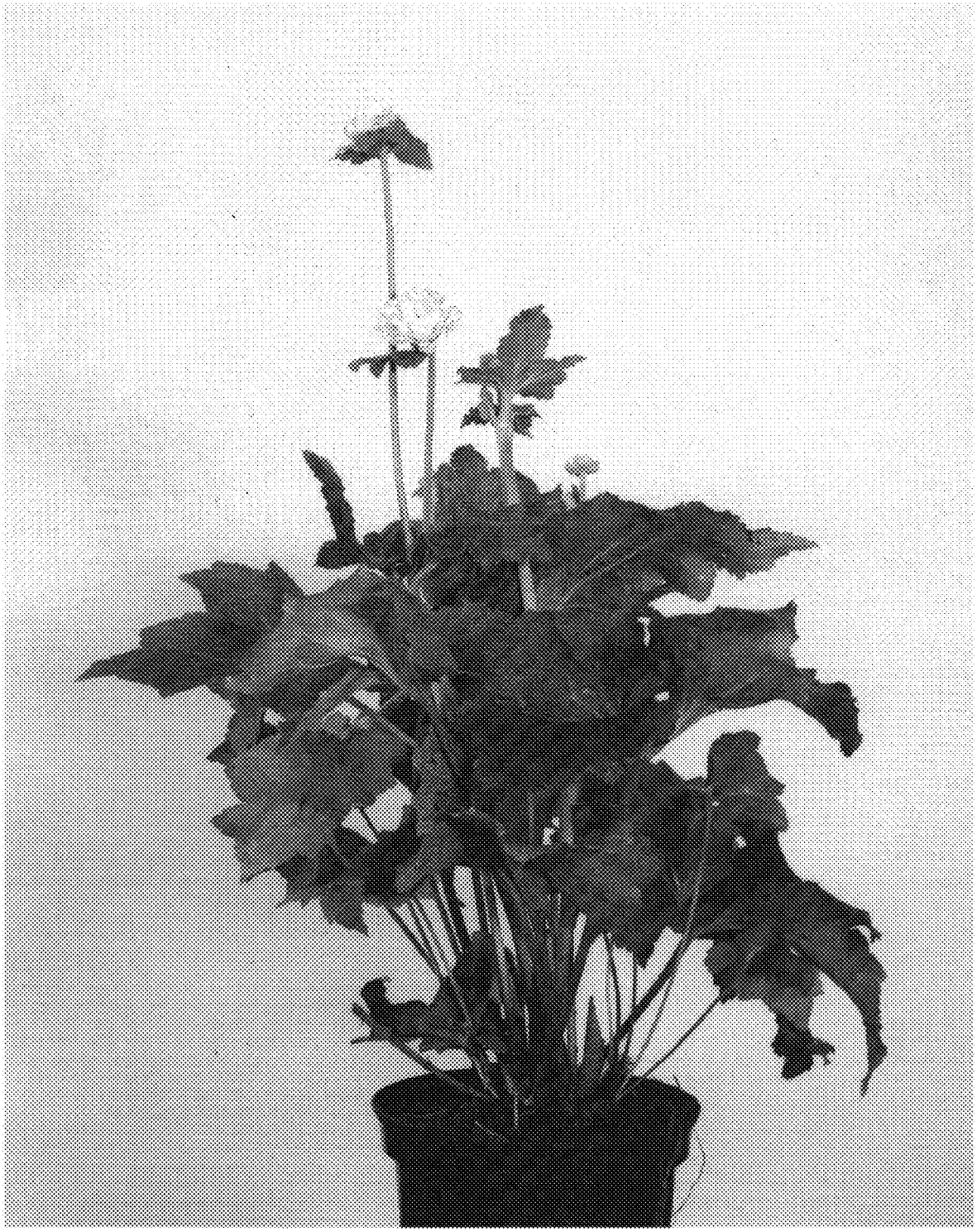
FIG. 1 shows, as nearly true as it is reasonably possible to make the same in color illustrations of this type, the typical foliage and growth characteristics of the new cultivar, 'WESKIPO'. The plant shown is approximately one year old, potted into a 19 cm nursery pot, grown outdoors in Kirkcudbright, Scotland at a commercial nursery.
Figure 2:
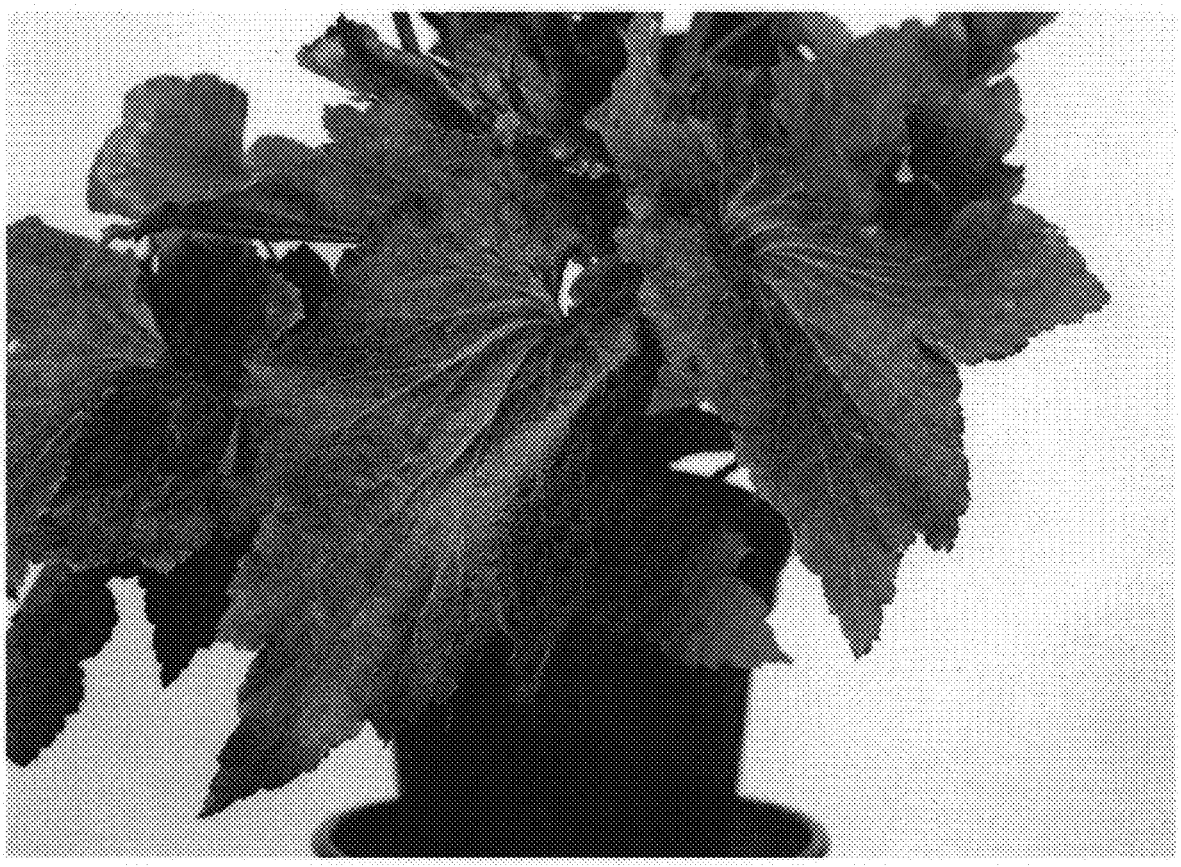
FIG. 2 shows, as nearly true as it is reasonably possible to make the same in color illustrations of this type, the typical foliage of the plant in FIG. 1.
Figure 3:
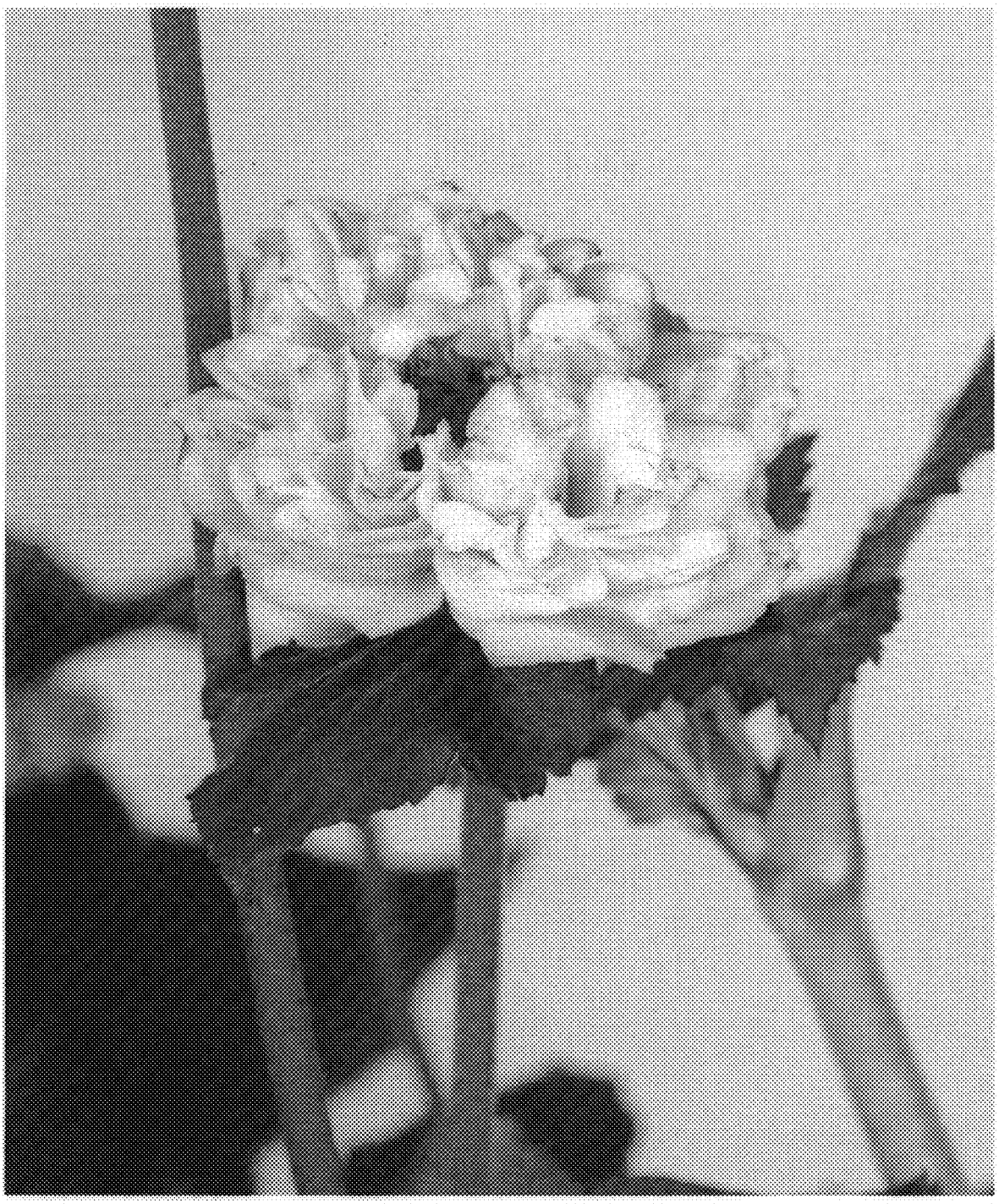
FIG. 3 shows, as nearly true as it is reasonably possible to make the same in color illustrations of this type, the typical flower of the plant in FIG. 1.

The following is a detailed botanical description of a new and distinct variety of *Anemone* hybrid known as 'WESKIPO', based upon observations of one year old plants, potted into 19 cm nursery pots and grown in a climate controlled greenhouse in The Netherlands. Plants were grown in full sun using accepted fertility and irrigation practices for *Anemone* plants. No chemical pest control measures were employed. Furthermore, no artificial light or photoperiodic treatments were given to the plants. Observation data was recorded in October of 2021.

Those skilled in the art will appreciate that certain characteristics will vary with older or, conversely, with younger plants. 'WESKIPO' has not been observed under all possible environmental conditions. Where dimensions, sizes, colors and other characteristics are given, it is to be understood that such measurements are approximations or averages set forth as accurately as practicable. The phenotype of the variety may differ from the descriptions set forth herein with variations in environmental, climactic and cultural conditions. Color notations are based on The Royal Horticultural Society Colour Chart, The Royal Horticultural Society, London, sixth edition, 2015.

A botanical description of 'WESKIPO' and a comparison with the parent, which is the most similar variety of common knowledge, is provided below.

General plant description:

*Growth habit.*—Herbaceous perennial with leaves developing from basal rosettes; flowering stems arising from the rosette also bear foliage; no lateral branching is present.

*Profile.*—Broad ovate to flattened globular.

*Growth rate.*—Moderately fast to fast growing.

*Plant vigor.*—Highly vigorous.

*Height.*—52.0 cm to the top of the foliar plane; 64.1 cm to the top of the floral plane.

*Width.*—62.3 cm.

*Propagation.*—Method — Root cuttings and meristematic tissue culture. Time to initiate rooting — Approximately 2 weeks at an average ambient temperature of 22 degrees Celsius. Time to produce flowering plant from rooted cutting — Approximately 6 to 8 weeks to produce a rooted young plant; 16 to 20 months to produce a marketable potted plant.

*Pest resistance and susceptibility.*—Plants have not been observed to be any more or less susceptible or resistant to pathogens and pests common to *Anemone* sp.

*Environmental tolerances.*—Adapt to, at least, USDA Zones 4 to 9 and temperatures ranging from minus 30 degrees Celsius to 35 degrees Celsius; moderate tolerance to rain; moderate tolerance to wind.

Root system:

*Type.*—Moderately fibrous root system.

*Branching.*—Very freely branched.

*Density.*—Moderately dense.

*Distribution.*—Roots distributed evenly throughout the soil profile, from shallow to deep.

*Texture.*—Smooth; lacking root hairs.

Stem:

*Branching habit.*—Basally branched; free branching.

*Number of primary (main) stems per plant.*—8.

*Number of secondary (lateral) branches per plant.*—None.

*Attitude.*—Near vertical; average angle of 15 degrees from vertical.

*Aspect.*—Elliptic.

*Length.*—34.0 cm, excluding the peduncle.

*Diameter.*—1.0 cm at the widest point, and 0.7 cm at the narrowest.

*Internode length.*—34.0 cm.

*Texture.*—Densely pubescent; 0.1-cm-long, adpressed hairs are short and thin and colored greyed-white, nearest to RHS 156D.

*Luster.*—Slightly glossy.

*Strength.*—Strong.

*Color, juvenile.*—Yellow-green, nearest to RHS 144A.

*Color, mature.*—Yellow-green, nearest to a mixture of RHS 146A and 146B.

*Color at internodes.*—Yellow-green, nearest to a mixture of RHS 146A and 146B.

Foliage:

*Arrangement.*—Leaves are borne both basally and on the flowering stems.

*Basal leaves.*—Attachment — Petiolate. Arrangement — Alternate. Division — Trifoliate. Compound leaf outline — Broadly ovate. Length — 30.4 cm. Width — 26.8 cm. Attitude — Upward and outward. Leaflets — Shape — Ovate to broad ovate. Length — Terminal leaflet is 19.7 cm long; lateral leaflets are 22.3 cm long. Width — Terminal leaflet is 12.5 cm wide; lateral leaflets are 14.6 cm wide.

Attitude — Outward, relative to the petiole. Aspect — Slightly to moderately carinate. Apex — Narrowly acute. Base — Truncate to hastate. Margin — Biserrate. Texture, adaxial surface — Sparsely to moderately covered with short, soft hairs with an average length of 0.075 cm; colored greyed-white, nearest to RHS 156D. Texture, abaxial surface — Sparsely to moderately covered with short, soft hairs with an average length of 0.075 cm; colored greyed-white, nearest to RHS 156D. Veins are densely covered with 0.1-cm-long hairs that are colored greyed-white, nearest to RHS 156A. Luster, adaxial surface — Slightly glossy. Luster, abaxial surface — Matte. Color — Juvenile color, adaxial surface — Yellow-green, nearest to RHS 144A. Juvenile color, abaxial surface — Green, nearest to a mixture of RHS 138B and 143B. Mature color, adaxial surface — Nearest to a mixture of green and yellow-green, RHS NN137A and 147A. Mature color, abaxial surface — Yellow-green, nearest to RHS 147B. Venation — Type — Laciniate. Vein color, adaxial surface — Yellow-green, nearest to in between RHS 144A and 144B. Vein color, abaxial surface — Yellow-green, nearest to RHS 147D. Petiole — Length — 23.6 cm. Diameter — 0.7 cm. Strength — Strong. Texture, adaxial and abaxial surfaces — Moderately covered with soft hairs; average length of hairs is 0.075 cm; colored greyed-white, nearest to RHS 156D. Luster, adaxial and abaxial surfaces — Slightly glossy. Color, adaxial surface — Yellow-green, nearest to a mixture of RHS 146A and 146B. Color, abaxial surface — Yellow-green, nearest to RHS 145A. Sheath — Length — 4.0 cm. Width — 0.8 cm. Color — Yellow-green, nearest to RHS 146B. Stipules — None present.

*Leaves of flowering stems.*—Attachment — Petiolate. Attitude — Outward. Arrangement — Opposite. Division — Simple. Shape — Ovate to broadly ovate; trilobate; lobes are deeply lobed to near-cleft. Lobes — Depth of sinuses — Varying from moderately deep to very deep. Sinus orientation — Convergent. Length — 14.6 cm. Width — 13.3 cm. Aspect — Slightly to moderately carinate. Apex — Narrowly acute. Base — Truncate to hastate. Margin — Serrate to biserrate. Texture, adaxial surface — Sparsely to moderately covered with short, soft hairs with an average length of 0.075 cm; colored greyed-white, nearest to RHS 156D. Texture, abaxial surface — Sparsely to moderately covered with short, soft hairs with an average length of 0.075 cm; colored greyed-white, nearest to RHS 156D. Veins are densely covered with 0.1-cm-long hairs that are colored greyed-white, nearest to RHS 156A. Luster, adaxial surface — Slightly glossy. Luster, abaxial surface — Matte. Color — Juvenile color, adaxial surface — Yellow-green, nearest to RHS 144A. Juvenile color, abaxial surface — Green, nearest to a mixture of RHS 138B and 143B. Mature color, adaxial surface — Nearest to a mixture of green and yellow-green, RHS NN137A and 147A. Mature color, abaxial surface — Yellow-green, nearest to RHS 147B. Venation — Type — Laciniate. Vein color, adaxial surface — Yellow-green, nearest to in between RHS 144A and 144B. Vein color, abaxial surface — Yellow-green, nearest to RHS 147D.

*Petiole.*—Length — 2.9 cm. Diameter — 0.55 cm. Strength — Strong. Texture, adaxial and abaxial surfaces — Moderately covered with soft hairs; average length of hairs is 0.075 cm; colored greyed-white, nearest to RHS 156D. Luster, adaxial and abaxial surfaces — Slightly glossy. Color, adaxial surface — Yellow-green, nearest to RHS 144B. Color, abaxial surface — Yellow-green, nearest to RHS 144B. Sheath — Length — 1.8 cm. Width — 0.6 cm. Color — Yellow-green, nearest to RHS 146D. Stipules — None present.

Inflorescence:

*Habit.*—Terminal compound cyme.

*Natural flowering season.*—Spring through late spring in Kirkcudbright, Scotland.

*Time to flower or response time.*—Approximately 10 months.

*Height.*—31.5 cm.

*Diameter.*—7.5 cm.

*Quantity of flowers per inflorescence.*—9, on average.

*Quantity of flowers per plant.*—33, on average.

*Quantity of flower buds per plant.*—60, on average.

*Quantity of flowers and flower buds per plant.*—63, on average.

*Peduncles.*—Length — Average of 24.2 cm. Diameter — Average of 0.4 cm. Angle — Average angle to the stem is approximately 10 degrees. Strength — Strong. Texture — Smooth. Pubescence — Densely covered with soft hairs; average length of hairs is 0.1 cm; hairs colored greyed-white, nearest to RHS 156A. Luster — Very slightly glossy. Color — Yellow-green, nearest to a mixture of RHS 146A; moderately to heavily suffused with a combination of greyed-purple, nearest to RHS N186C, and brown, nearest to RHS 200B.

Bud:

*Shape.*—Flattened.

*Length.*—Average of 1.3 cm.

*Diameter.*—Average of 2.1 cm.

*Texture.*—Smooth and dense wooly pubescence; hairs with an average length of 0.1 cm and colored greyed-green, nearest to a mixture of RHS 193B, 193C, and 193D.

*Luster.*—Matte.

*Color.*—Yellow-green, nearest to RHS 144C.

Flower:

*Conformation.*—Rotate, semi-double apetalous flowers.

*Aspect.*—Upright to slightly outward.

*Flowering habit.*—Moderately free-flowering.

*Flower Longevity on plant.*—Approximately 10 days.

*Persistent or self-cleaning.*—Self-cleaning.

*Fragrance.*—Non-fragrant.

*Diameter.*—Average of 6.6 cm.

*Depth.*—Average of 3.1 cm.

*Tepals.*—Quantity — Average of 7; occasionally 8. Arrangement — Rotate; the unfused tepals arranged in 2 whorls. Length — 2.9 cm. Width — 1.8 cm. Shape — Obovate. Apex — Obtuse to bluntly acute. Base — Cuneate. Margin — Entire; no undulation to slightly undulated. Texture, luster and pubescence of the upper surface — Glabrous, matte, and velvety. Texture, luster and pubescence of the lower surface — Smooth, slightly glossy, and densely covered with appressed soft, silky hairs; average length of hairs is 0.1 cm; colored white, RHS NN155D. Color — When opening, upper surface — Green-white, nearest to RHS 157A, and fading lighter towards the margins and apex, nearest to RHS 157D; apex is suffused with purple, nearest to RHS 75A. When opening, lower surface — Yellow-green, nearest to in between RHS 145C and 145D; apex is lightly suffused with purple, nearest to RHS 76D. Fully opened, upper surface — Green-white, nearest to RHS 157A, and fading lighter towards the margins and apex, nearest to RHS 157D; apex is suffused with purple, nearest to RHS 75A. Tepal color does not fade. Fully opened, lower surface — Yellow-green, nearest to in between RHS 145C and 145D; apex is suffused with purple, nearest to RHS 73D. Tepal color does not fade. Tepal venation — Fully opened, upper surface — No venation is visible. Fully opened, lower surface — Yellow-green, nearest to in between RHS 145C and 145D.

*Tepaloids.*—Quantity — Average of 90. Arrangement — Rotate; the unfused tepaloids arranged in 10 whorls. Length — 2.7 cm. Width — 1.0 cm. Shape — Variable; oblanceolate to narrowly obovate, and occasionally slightly falcate. Apex — Acute to bluntly acute. Base — Narrowly cuneate. Margin — Entire; slight coarse undulation. Texture, luster and pubescence of the upper surface — Velvety, very slightly glossy, and glabrous. Texture, luster and pubescence of the lower surface — Smooth, very slightly glossy, and densely covered with appressed soft, silky hairs; average length of hairs is 0.1 cm; colored white, RHS NN155D. Color — When opening, upper surface — Green-white, nearest to RHS 157B, and fading lighter towards the margins and apex, nearest to RHS 157D; apex is suffused with purple, nearest to RHS 75B. When opening, lower surface — Green-white, nearest to RHS 157B, and fading lighter towards the margins and apex, nearest to RHS 157D; apex is suffused with purple, nearest to RHS 75C. Fully opened, upper surface — Purple, nearest to RHS 75D; base is green-white, nearest to RHS 157D. Tepaloid color does not fade. Fully opened, lower surface — Purple, nearest to RHS 75D; base is green-white, nearest to RHS 157D. Tepaloid color does not fade. Tepal venation — No visible venation on the upper or lower surfaces.

*Pedicels.*—Flowers sessile.

Reproductive organs:

*Stamens.*—Quantity — Approximately 200. Anthers — Shape — Oblong. Length — Approximately 0.2 cm. Width — Approximately 0.15 cm. Color — Yellow, nearest to RHS 13B. Filaments — Length — 0.7 cm, on average. Color — White, nearest to RHS 155A. Pollen — Color — Yellow, RHS 11D. Abundance — Sparse.

*Pistil.*—Quantity — Approximately 500. Length — 0.115 cm. Style — Length — 0.095 cm. Color — Yellow-green, nearest to RHS 145B. Stigma — Shape — Club-shaped. Dimensions — 0.02 cm long and 0.02 cm in diameter. Color — Yellow-green, nearest to RHS N144A. Ovary Color — Yellow-green, nearest to RHS 145D.

Seed and fruit: No fruit or seeds have been detected to date.

Comparisons with the parent plants: Plants of the new cultivar 'WESKIPO' may be distinguished from its parent and most similar commercial variety, *Anemone hupehensis* 'Lorelei' (unpatented), by the characteristics described in Table 1.

TABLE 1

| Characteristic | 'WESKIPO' | 'Lorelei' |
|---|---|---|
| Growth habit. | More compact than 'Lorelei'. | Less compact than 'WESKIPO'. |
| Foliage and flowering stem strength. | Stronger than 'Lorelei'. | Weaker than 'WESKIPO'. |
| General coloration of the mature foliage. | Lighter green, relative to'Lorelei'. | Darker green, relative to 'WESKIPO'. |
| Flower conformation. | Apetalous flowers with an abundance of tepaloids. | Apetalous flowers with tepals and fewer tepaloids. |

That which is claimed is:

1. A new and distinct variety of *Anemone* plant named 'WESKIPO', substantially as described and illustrated herein.

* * * * *